United States Patent [19]
Russo et al.

[11] Patent Number: 5,255,422
[45] Date of Patent: Oct. 26, 1993

[54] SCALPEL BLADE ON-OFF TOOL

[76] Inventors: Ronald D. Russo, 8 Candleberry Rd., Barrington, R.I. 02806; Nancy A. Coyne, 85 Spring Lake Dr., DeBary, Fla. 32713

[21] Appl. No.: 977,784

[22] Filed: Nov. 17, 1992

Related U.S. Application Data

[63] Continuation-in-part of Ser. No. 751,859, Aug. 29, 1991, abandoned.

[51] Int. Cl.⁵ ............................................ B23P 19/04
[52] U.S. Cl. ....................................... 29/268; 29/270; 29/278; 269/6; 81/426
[58] Field of Search ................ 29/244, 242, 267, 268, 29/270, 278, 281.6, 248, 283; 269/6; 81/426, 419, 424.5; 606/205-210, 167, 174

[56] References Cited

U.S. PATENT DOCUMENTS

| | | | |
|---|---|---|---|
| 851,906 | 4/1907 | Burger | 81/426 |
| 3,812,743 | 5/1974 | Shaw et al. | 29/268 |
| 4,372,182 | 2/1983 | Kolter | 81/426 |

Primary Examiner—Bruce M. Kisliuk
Assistant Examiner—Eileen P. Morgan
Attorney, Agent, or Firm—Robert J. Doherty

[57] ABSTRACT

A tool for both attaching and removing surgical scalpel blades safely from any standard surgical scalpel handle. The tool taking the form of hand held normally open pliers with an upper jaw including a clear protective cover and a protruding lower jaw. The lower jaw includes a recessed slot and two protrusions for accepting any scalpel blade. Closure of the upper jaw holds the tip of the blade in place while the protruding lower jaw holds the scalpel blade in place for either attachment or removal of the blade from the handle. An alternate embodiment of the tool especially designed as a single use disposable is also included.

33 Claims, 4 Drawing Sheets

SCALPEL BLADE ON-OFF TOOL

This application is a continuation-in part of U.S. patent application Ser. No. 07/751,859 filed Aug. 29, 1991, now abandoned.

BACKGROUND AND OBJECTS OF THE INVENTION

In the U.S., Britain and other western countries, there is a standard for surgical scalpel handles and detachable scalpel blades. The handles are designed to be reusable and the blades sterile packaged and disposable after use. There are three standard handles which are No. 4 (large style), No. 3 and No. 7 (small styles). The No. 4 handle accepts any twenty series (Nos. 20, 21, 22) disposable blades while the No. 3 and No. 7 accept any teen series (Nos. 10, 11, 15) disposable blades.

Reference is made to U.S. Pat. No. 3,812,743 to Shaw et al which gives an accurate description of scalpel handle and blade configurations and engagements using British standard 2982:1958. In this regard, the disclosure of U.S. Pat. No. 3,812,743 is incorporated into the subject disclosure by specific reference. The tool of Shaw was never commercialized since it suffered from several limitations. First, it could only accept either twenty series or teen series blades, but not both. Two separate tools would therefore have been required. Secondly, it would not function well for applying blades onto the handle because the upper and lower jaws completely enclosed the blade so the operator could not visibly see the engagement slot on the blade to facilitate engagement. The major problem with the Shaw device, however, would be its tendency to fracture blades due to the channel members on the jaws completely sandwiching the blades such that blades would snap in two presenting a danger to the user. The Shaw device, however, represents an initial attempt at a hand held device for handling standard blades and handles.

While Shaw's device locked the blade over its entire length in an upper and lower jaw, U.S. Pat. No. 3,825,990 to Shields describes a version where only the blade tip is gripped, and a separate lever is used to lift up the back of the blade. This would permit the hardened steel scalpel blade to flex. Shield's device is rather crude and has to use special blades with a rear tab for lifting up the blade. Flexure of the blade, however, would appear to prevent the blade fracturing drawback of the Shaw device.

More recently, Machida U.S. Pat. No. 4,922,614 took the approach of developing a special handle and blade. However, both the devices of Shields and Machida do not address a solution to the problem of ease of attachment and removal of standard handles and blades.

The safe handling of surgical blades and especially used contaminated blades is very important since infection to surgeons and operating room nurses can readily occur if they are cut handling used blades. A recent study from the Center for Disease Control indicated that surgical personnel are at significant risk for contracting HIV (AIDS) or hepatitis while handling used surgical blades (sharps).

BRIEF SUMMARY AND OBJECTS OF THE INVENTION

With the foregoing in mind, the present invention offers a safe, easy to use tool for both applying and removing scalpel blades in all sizes of handles and blades.

The present invention protects users from accidentally cutting themselves during blade handling and reduces the likelihood of infection from blood born diseases such as HIV (AIDS) or hepatitis.

Accordingly, it is the primary object of the invention to provide a safe, easy to use, hand-held tool that can apply and remove any standard blade.

Another object is to provide a device which can either be reusable or disposable after use either by making the product from inexpensive materials or by reducing its component parts to as few as two parts in one of the embodiments of the invention.

Another object is to provide a device which prevents fracture of the blade during use.

Another object is to provide a device which can be used by only one hand and is normally open and ready for use.

Another object is to provide a protective cover to protect the user's eyes if a blade prematurely fractures and fragments become air born.

Another object of the present invention is to provide a tool wherein only two components, both preferably injection molded from plastic, are utilized to reduce cost and to produce a tool requiring minimal assembly of the two molded components to produce a tool which is very inexpensive to manufacture and can therefore be sold at a very low price making it convenient to be disposable after use.

Another object is to produce an inexpensive plastic molded tool which can be prepackaged and sterilized and sold ready for use in an operating room environment.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention.

DESCRIPTION OF THE PREFERRED EMBODIMENT

Figure 1:
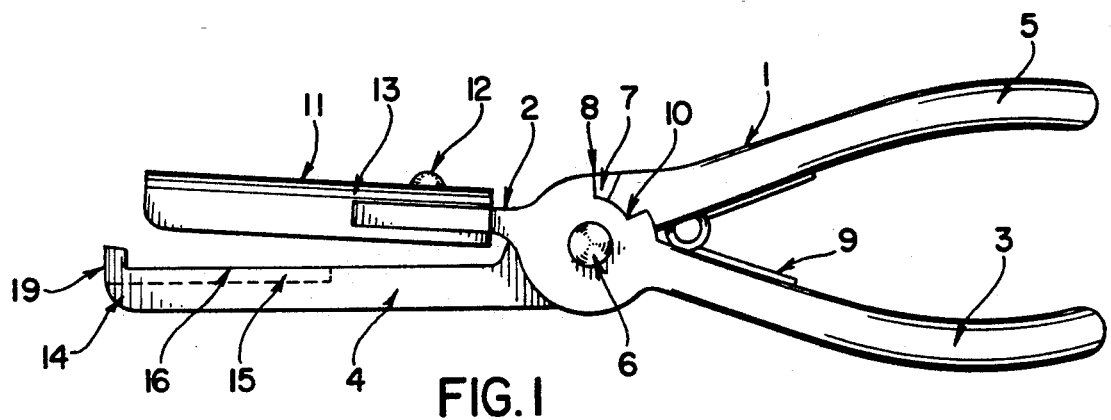
FIG. 1 is a side view of the device including its protective clear cover.

As shown in FIG. 1, the assembled tool 1 includes an upper jaw 2 which is formed as part of lower handle 3. The lower jaw 4 is formed as a part of the upper handle 5. Upper jaw and lower jaw are pivotally connected at cross pin 6. An integral stop 7 is part of lower jaw 4 and normally rests against front recess 8 formed as a part of upper jaw 2. Snap spring 9 holds both jaws normally open and stop 7 is normally positioned against recess 8. When the handles 3 and 5 are manually squeezed closed, then stop 7 will rest against back recess 10 also formed as part of upper jaw 2.

A separate molded clear plastic protective cover 11 is attached to the upper jaw by rivet 12. The upper jaw 2 ends at terminal edge 13, but the lower jaw 4 extends outwardly to a terminal edge 14. Formed as a part of the lower jaw is slotted recess 15 which is recessed about .060 inches below the lower jaw upper surface 16. Such upper surface 16 can either be cut or molded to form the recess 15 or a lower surface, in effect, built up as by side walls to form the recess between such side walls. The slotted recess 15 is more clearly shown in FIG. 2. Essentially, the entire lower jaw is visible from above, that is, from the operator's viewpoint, through clear cover 11. Slotted recess 15 also extends a length of 1.125 inches along the lower jaw. The above dimensions, that is, the recess length and depth, have been found to be ideal to accept the large No. 4 scalpel handle.

Figure 3:
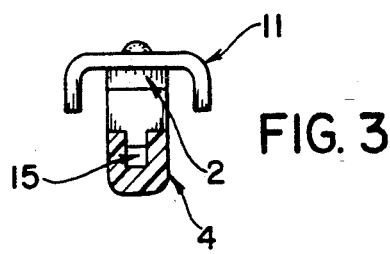
FIG. 3 is a sectional view taken along line 3—3 of FIG. 2.
Figure 5:
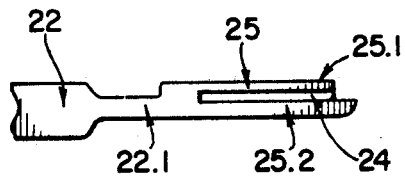
FIG. 5 is a fragmentary side view of a scalpel handle distal portion ready for engagement onto a scalpel blade as shown in FIG. 4.
Figure 4:
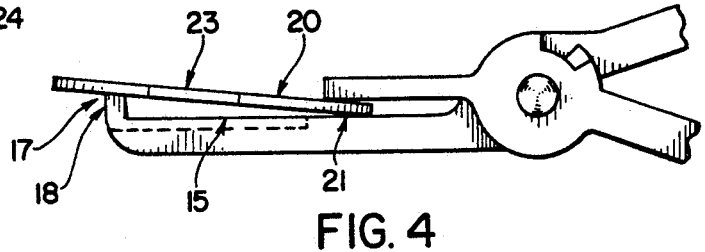
FIG. 4 is a fragmentary side view of the device holding a scalpel blade ready for attachment to a handle.

A pair of protrusions 17 and 18 form an upward extension of the lower jaw terminal edge 14. These protrusions rise above surface 16 about 0.090 inches which has been found to be ideal for lifting off scalpel blades. A ledge face 19 formed by the lower jaw portions and protrusion portions extending above the terminal edge 14 acts as an insertion stop when handles with blades are inserted into the lower jaw recess. Also, the protrusions upwardly terminate in generally flat surfaces 32 which are adapted to engage the rear portions of blades as will hereinafter be more evident. FIG. 3 shows a clear cross-sectional view of lower jaw 4, upper jaw 2, recess 15, and clear cover 11. FIG. 4 shows a typical scalpel blade 20 being firmly gripped by both upper and lower jaws only at its tip 21 and in its natural position ready for engagement by the scalpel handle 22 as shown in FIG. 5.

The scalpel handle 22 includes a forwardly projecting narrow extension 22.1 having a pair of inwardly extending slots 24 so as to define an upwardly extending shoulder 25. Scalpel blade slot 23 is ready for engagement into matching opposed slots 24 on handle 22. Such standard scalpel handles include a forwardly extending shoulder 25 divided into upper and lower segments 25.1 and 25.2 respectively by slots 24. Generally, the shoulder segments are of equal width and thus form a narrow extension of the handle 22. On large No. 4 scalpels, the shoulder 25 is 0.140 inches wide while on small handles No. 3 and No. 7, the shoulder 25 is 0.100 inches wide. It has been discovered that the ideal width for recessed slot 15 is 0.145 inches wide which is just wide enough to accept the large shoulder yet plenty large enough to accommodate the smaller shoulder on No. 3 and No. 7 scalpels. Protrusions 17 and 18 adjacent the recess 15 thus are separated only by the 0.145 inch ideal width of the recess slot such that they clearly serve to clearly lift off both large and small scalpel blades as will hereinafter be apparent.

Figure 6:
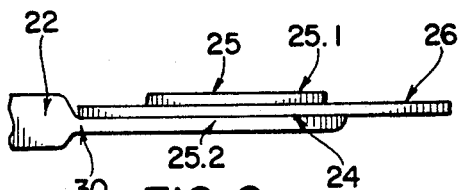
FIG. 6 is a fragmentary side view of a scalpel handle with a blade attached.
Figure 7:
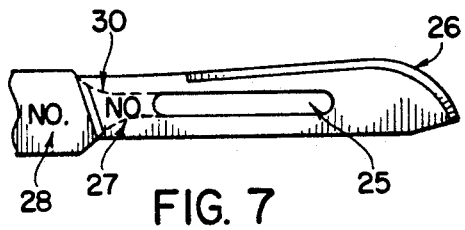
FIG. 7 is a fragmentary top view of a scalpel handle with a blade attached.

Scalpel blade 26 is shown already attached to handle 22 in FIG. 6. Shoulder 25 is more clearly shown in top view in FIG. 7. All blades are marked with their number size as shown in 27. To insure proper engagement, both the blade number 27 and the handle number 28 must both face upwards during engagement on the tool.

Figure 8:
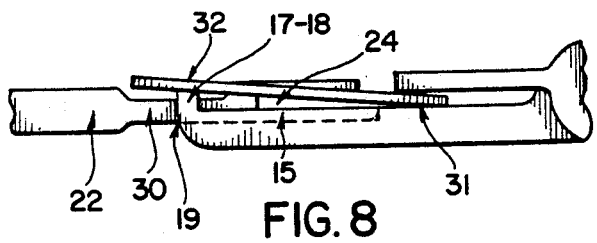
FIG. 8 is a fragmentary side view of the device showing a scalpel being lifted off the scalpel handle.

As noted in FIG. 8 when a bladed scalpel handle 22 is inserted into slotted recess 15, it has an outwardly facing curved surface 30 which is stopped at ledge 19. This acts as a positive stop to the user to gauge the depth of insertion of the scalpeled blade. Thereafter, the jaws are closed, and they firmly grip the tip of the scalpel blade at 31. Clamping of the jaws automatically engages protrusions 17 and 18 to lift up the rear of the scalpel at surface 32. To better show this, FIGS. 4 and 8 are shown without the cover. Lifting the scalpel blade at the rear surfaces 32 disengages the blade from slot 24 on the handle. Simple retraction of the handle 22 backwards will remove the handle from the blade. The blade remains captured in the jaws of the tool at point 31. Safe deposit of the blade can be made by using a blade safety deposit box as disclosed in our co-pending patent application.

The tool can be made reusable and autoclavable by being made of forged stainless steel and having a molded clear polycarbonate protective cover. If desired, it can be injection molded in a three-piece assembly of lower jaw, upper jaw, and clear cover to be disposable. Both jaws could be molded from any engineering thermoplastic material as well as the cover.

Figure 9:
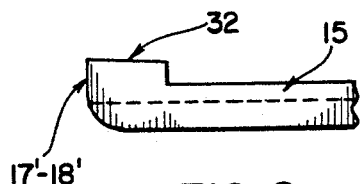
FIG. 9 is a fragmentary side view of the lower jaw showing an alternate design of the lower jaw protrusions.

FIG. 9 shows an alternate design of protrusions 17' and 18' where the top surface 32 can be tapered downward on a flat surface to give the blade more engagement area.

Figure 10:
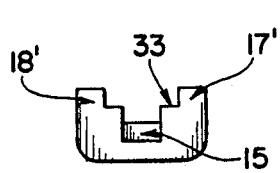
FIG 10 is an end view of the alternate lower jaw design.

As shown in FIG. 10, a shallow recess 33 can also be provided in protrusions 17 and 18 to help manual positioning of the rear of the scalpel blade and to prevent the blade from moving laterally. This is especially useful when sliding slot 24 on the handle into mating slot 23 of the blade. The recess 33 need only be 0.020 inches deep and 0.270 inches wide to accommodate all blades.

Figure 1A:
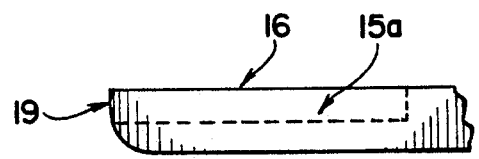
FIG. 1A is a partial side view similar to FIG. 1 but showing a modification thereof.

In FIG. 1A, the tool is shown in perhaps its simplest form, that is, without the presence of the protrusions 17 and 18. In such form, it should be pointed out that it is necessary to increase the depth of the recess 15A over the depth of the recess 15 shown in the other FIGS. since without the protrusions it is necessary to push or otherwise move the scalpel handle extension initially downward to force the blade off its attaching shoulder before retracting the handle outwardly, that is, to the left as depicted in the drawings. Thus recess 15A should be at least 0.090 inch in depth or an increase of about 0.030 inch over that of recess 15. This would provide for about 0.30 inch lift off for the blade when supported flatly against the upper surface 16 of the lower jaw assuming about 0.060 inch thickness for the handle extension. Thus when no protrusions are utilized, it is necessary for the operator, once he or she has placed the bladed scalpel in position and moved the jaws to their closed position which grips the distal portion of the blade, to push down on the handle so as to move the extension shoulder past the blade which is unable to move because of its support by surface 16. This movement frees the blade from its engagement in the slots 24 and thereafter enables complete disassembly of the handle from the blade by then simply rearwardly withdrawing the handle. Thus without protrusions, the operator must perform a two-step motion (downward then rearward) to accomplish disassembly while in those preferred forms utilizing protrusions only a rearward motion (one step motion) is required since the elevation of the proximal blade end is automatically accomplished by the protrusions when the jaws are moved to their closed blade clamping position. In assembling the blade to the handle, the motions and the sequence are simply reversed.

As can be seen from the above description with specific respect to FIGS. 1-11, the tool assembly and structure is depicted as a reusable tool, although it is noted that the components could be made disposable by molding them in plastic. However as seen in FIG. 1, the assembly would have at least six different parts all requiring considerable fixturing and assembly time and labor to manufacture making the device too expensive as a disposable item in the commercial marketplace. Thus it would be desirable to devise a tool with all the functional aspects of the original device in a much less expensive product yet still meet all the objects of this reusable device.

Figure 12:
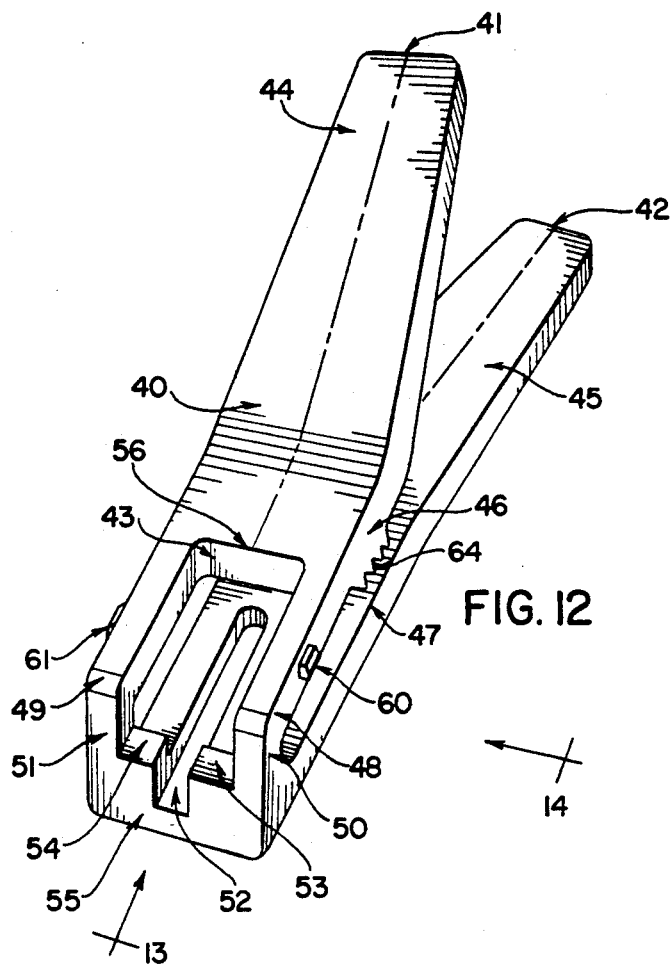
FIG. 12 is a perspective view of an alternate embodiment of the invention specifically designed for single use showing the molded one-piece body of the device without its protective cover.
Figure 13:
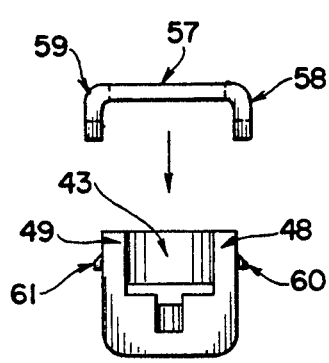
FIG. 13 is a front end view taken from arrow direction 13 in FIG. 12 showing the cover ready to be assembled onto the molded body.
Figure 14:
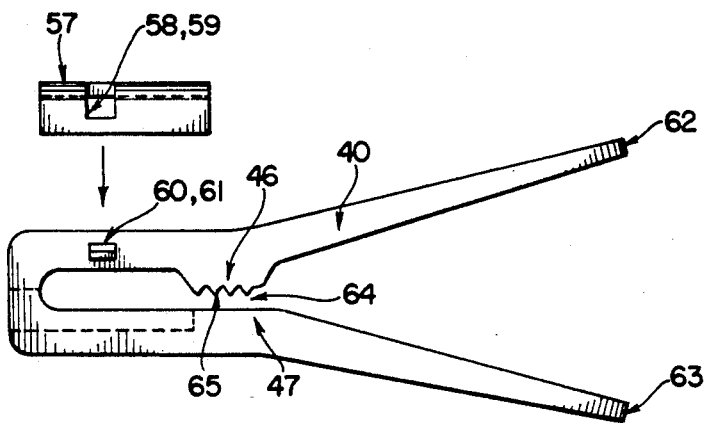
FIG. 14 is a side view of the device taken from arrow direction 14 in FIG. 12 also showing the cover ready to be assembled onto molded body.

With the foregoing in mind, the alternative embodiment shown in FIGS. 12-14 provides a tool for both applying and removing scalpel blades comprising just two components.

As shown in FIG. 12, the tool includes a one piece preferably injection molded plastic body 40 molded along parting lines 41 and 42. Opening 43 in the tool is formed as part of the injection molded body. The upper handle 44 and lower handle 45 are molded as part of the tool. Also formed as part of the tool is upper jaw 46 and lower jaw 47.

It should be apparent that the operational relationship or positioning of the upper and lower jaws with respect to each other shown in FIGS. 12 and 14 is that the essential operating portion of the lower jaw is substantially longer than the essential operating portion of the upper jaw as in the previously disclosed embodiment. However since the upper jaw is hingedly connected to the lower jaw at the front or distal end of the device, a pair of side arms 48 and 49 project forwardly from the forward terminus of the upper jaw to connect such at points or posts 50 and 51. Accordingly as used for descriptive purposes of this application, the upper jaw, in essence, terminates at the base of slot 43 or at point 56 as will hereinafter be more fully brought out. Thus as in the previous embodiment, lower jaw 47 is substantially longer than upper jaw 46. Integrally molded-in side arms 48 and 49 are located in the front distal end of the device. Side arms 48 and 49 are slightly flexible at points 50 and 51 respectively. The posts or points 50, 51 and the side arms 48, 49 cooperate to form a frontal pivotal juncture.

The upper jaw 46 and lower jaw 47 are molded in a normally open position so there is a gap 64 formed between both jaws. When upper handle 44 and lower handle 45 are squeezed by the user, both side arms 48 and 49 will slightly flex at points 50 and 51 to close upper and lower jaws firmly together. A slight releasing grip on the handles will return the gap 64 to its original open position.

The body is ideally molded in one piece from rigid polypropylene which has a slight flexure modulus which will permit the ideal flexure of the side arms yet produce a very high compression force in the jaw areas. The tool is dimensioned such that the handles will preferably deliver a four to one compression ratio in the jaw areas which will firmly and securely grip the scalpel blade inserted into the jaws of the device.

Formed as part of lower jaw 47 is recess slot 52 and projections 53 and 54. The recess slot 52 is identical in function to slotted recess 15 shown in FIG. 2. Projections 52 and 53 also function identically to projections 17 and 18 depicted in FIG. 2.

Figure 2:
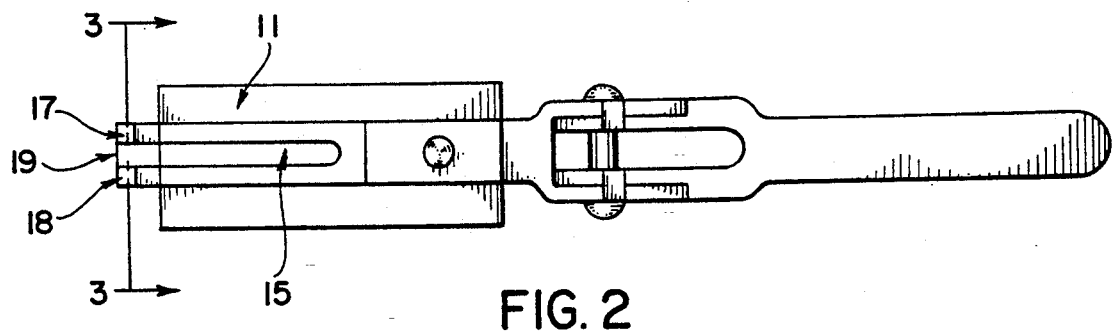
FIG. 2 is a top view of the device shown in FIG. 1.

Also as above noted, the lower jaw 47 extends beyond upper jaw 46 and terminates at distal end 55 and the upper jaw 46 is substantially recessed back from lower jaw 47 and terminates at point or surface 56. As such, the one piece molded body provides all the functional elements of the original embodiment as shown in FIGS. 1 and 2 with the exception of the clear or at least translucent molded protective cover. However, the one piece molded body eliminates the need for all the separate and individual components of the reusable device and all the fixturing and assembly time and labor.

FIG. 13 is an end view of the disposable tool showing opening 43 which is preferably about 0.570 inches wide to accept even the largest width scalpel blade. The clear protective cover 57 is preferably injection molded as a separate part from polystyrene, polycarbonate or some other suitable material. Molded on both sides of cover 57 are openings 58 and 59. Correspondingly, two tabs 60 and 61 are molded in on side arms 48 and 49. FIG. 14 clearly shows a side view of the body and cover ready for assembly. The clear cover is simply snapped over the side arms of the body such that the cover openings will self align themselves with tabs 60 and 61 on the side arms. Once snapped into place, the tabs will prevent the cover from being removed. The cover to body assembly takes only a second to snap into place.

Figure 11:
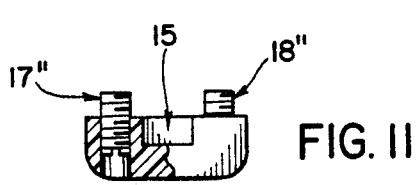
FIG. 11 is an end view of another alternate lower jaw design.
Figure 9A:
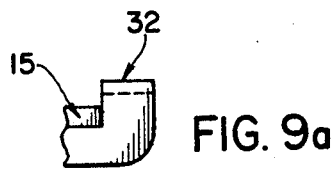
FIG. 9A is a partial end view of FIG. 9.

As shown in FIG. 14, molded-in ridges 65 can be formed as part of upper jaw 46 to provide additional compression force on an inserted blade tip. This disposable tool shown in FIGS. 12-14 will do everything the reusable tool shown in FIGS. 1-11 will do at a fraction of the cost. In its finished molded form, the disposable tool is designed to be hand held and be about 1 inch wide by 5 inches long and about 2 inches high from handle tip to handle tip 62 and 63 and weigh less than one ounce. It is so inexpensive and convenient to use that it can be used throughout the entire operating procedure on one patient and then discarded after use without the need for cleaning and re-use. Other configurations for the protrusions can be used such as rounded pins or square lugs and the protrusions can be either integral with the lower jaw or formed as attachments thereto as by the use of a pair of screws threadably recessed in bores formed in the lower jaw as shown in FIG. 11. Many variations and different embodiments may be selected without departing from the spirit and scope of the invention. One such specific variation is orienting the upper and lower jaws of the various embodiments crosswise to the handles such as shown in FIGS. 4 and 5 of the Shaw et al patent.

Figure 16:
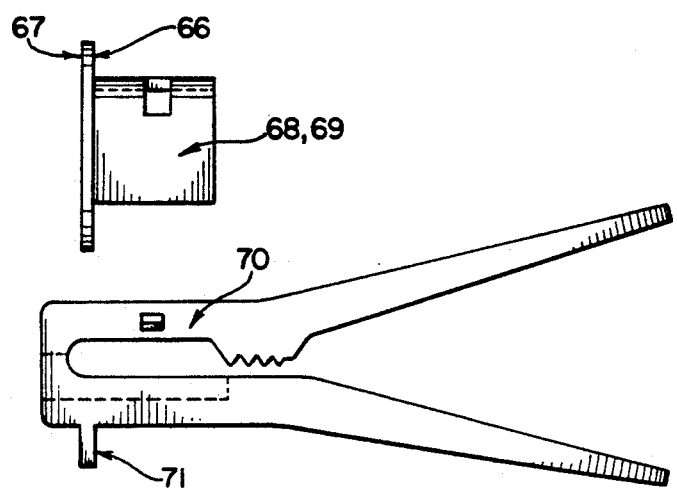
FIG. 16 is a side view of FIG. 15.
Figure 17:
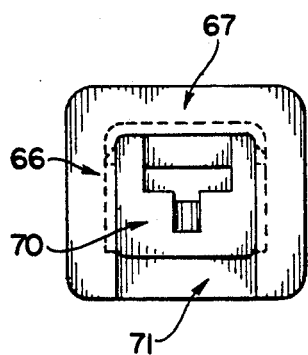
FIG. 17 is a front end view of the alternate version of the device showing the flanged clear cover assembled onto the molded body.
Figure 18:
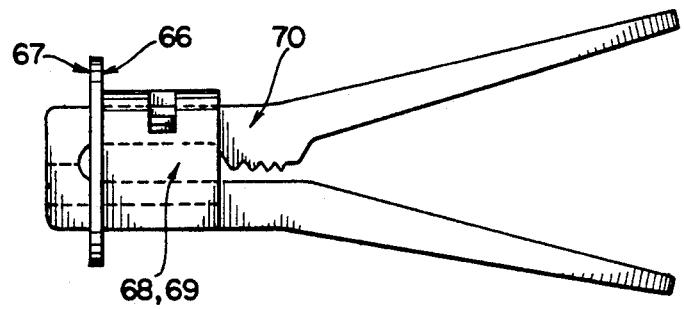
FIG. 18 a side view of FIG. 17.

An alternate version of the disposable embodiment of the device shown in FIGS. 12-14 is shown in FIGS. 16-18 wherein a flanged protective guard is provided to further protect the user's hand from any contact with the blade during insertion of the scalpel blade into the device. The flanged protective hand guard can be formed as part of the injection molded cover and body.

Figure 15:
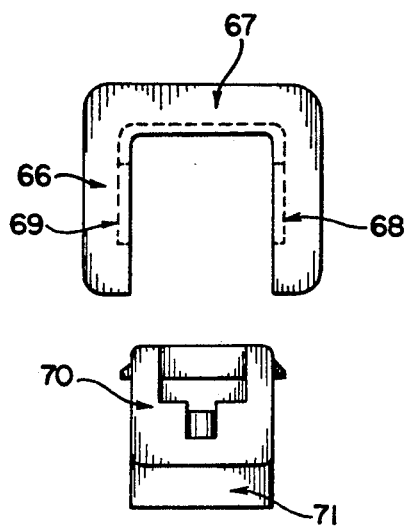
FIG. 15 is a front end view of an alternate version of the device shown in FIGS. 12-14 wherein a flanged clear cover ready to be assembled onto the molded body is shown.

FIGS. 15 and 16 show a flanged injection molded cover 66 formed with an outwardly extending flange 67 formed along the top and both sides of the cover. The cover 66 also has downwardly extending side walls 68 and 69. The injection molded body 70 has a lower flange 71 formed as part of its underside.

FIGS. 16 and 17 depict the clear cover 66 assembled onto body 70 using the same type of cover opening and tabs as on the body shown in FIGS. 13 and 14. As shown in FIG. 17, the combination of the three-sided flange 67 on the cover and the lower flange 71 on the body form a fully protective flange along all four sides of the device. The downwardly and outwardly extending side walls 68 and 69 also protect the user's hands from a misdirected blade. This alternate version gives added hand protection and security to the user without adding to the cost of the disposable embodiment of the device.

It should also be brought out that the threesided flange 67 could be altered to include the lower flange 71, that is, that the separately molded flange 67 include both sides and the bottom, and that a top flange be molded directly into the body 70. It is also possible that either of these above type protective flange configurations could be incorporated into the device shown in FIGS. 1-11.

While there is shown and described herein certain specific structure embodying this invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A tool for safely handling detachable blades of a removable blade scalpel wherein the blades include upper and lower opposed surfaces and an attachment slot, and the scalpel having a handle with a narrow forwardly projecting extension in turn having an upwardly projecting shoulder defined by a pair of inwardly directed longitudinally extending slots along said extension wherein said shoulder is adapted to receive the longitudinally directed attachment slot of a detachable blade, said tool comprising upper and lower longitudinally oriented jaws each having a distal and a proximal end connected for relative motion towards and away from each other to closed and open positions respectively, said lower jaw having a generally planar top surface adapted for engageable receipt of the lower surface of said blade with the distal end of said blade positioned between the proximal end portions of said jaws, said lower jaw being substantially longer than said upper jaw and a slotted recess formed in said lower jaw for receiving and repositioning said scalpel handle extension and for positioning said scalpel blade distal end for compressible engagement solely between said upper and lower jaw proximal ends in said closed position thereof, said lower jaw terminating at its outer distal end in a terminal face and said slotted recess extending through said terminal face and extending along a significant portion of said lower jaw.

2. The tool of claim 1, said lower jaw distal terminal face forming a stop surface against which the handle of said scalpel abuts while permitting access to the narrow forwardly projecting extension thereof into said recess.

3. The tool of claim 1, said recess extending inwardly along said lower jaw and terminating at an inner point proximal to but outwardly disposed of the terminal end of said upper jaw.

4. The tool of claim 1, said recess of a length equal to or greater than the length of the handle narrow extension of a No. 4 scalpel to be utilized therewith.

5. The tool of claim 1, said recess of a depth equal to or greater than that of the forward extension of the largest scalpel to be utilized therewith.

6. The tool of claim 5, said jaws normally spring biased to an open non-blade gripping position.

7. The tool of claim 6, said protrusions integral with said lower jaw.

8. The tool of claim 6, said protrusions being threaded members received in bores disposed through said lower jaw distal end.

9. The tool of claim 6, the support surfaces of said protrusions being upwardly outwardly slanted so as to form a greater contact surface for blades disposed at an angle between said jaws.

10. The tool of claim 9, said protrusions including a secondary stepped recess for lateral contact with the blade proximal portions to prevent lateral movement thereof.

11. The tool of claim 6, said protrusions extending upwardly to form a continuation of said lower jaw distal terminal face.

12. The tool of claim 1, said jaws having hand grips wherein the operator grips the hand grips to operate the device.

13. The tool of claim 1 including a pair of laterally-spaced protrusions upwardly extending above the upper surface of said lower jaw and positioned adjacent to and on either side of said recess at the distal end thereof, said protrusions upwardly terminating in generally planar support surfaces which in turn contact proximal portions of the scalpel blade so as to upwardly cant said blade so as to lift it off the handle shoulder while the distal end of the blade is held by the jaws when in their closed position.

14. The tool of claim 1, said upper jaw including a cover attached thereto and extending forwardly from said upper jaw terminal end over at least a major portion of said lower jaw recess, said cover being at least translucent such that said recess is visible during operation of the tool.

15. The tool of claim 1, said upper jaw having proximal and distal ends, a pivot arm forwardly extending from the distal end of said upper jaw and in turn terminating at a frontal pivotal juncture in turn connected to the lower jaw such that when the handles are compressed the juncture permits compressible engagement of the upper jaw with the lower jaw to engage a scalpel blade inserted between the upper and lower jaws.

16. The tool of claim 15 including a pair of upward protrusions positioned adjacent to and on either side of the entrance insertion slot on the lower jaw which lift off the blade on the scalpel when the upper and lower jaws are compressibly engaged.

17. The tool of claim 15, said jaws normally biased by the frontal pivotal juncture to a normally open non-blade gripping position.

18. The tool of claim 15 wherein the tool is of integral one piece molded plastic construction.

19. The tool of claim 1 including a cover positioned over the entrance insertion slot on the lower jaw, the cover being at least translucent such that the slot is visible during operation of the tool.

20. The tool of claim 1 wherein at least one of said jaws is provided with a blade deflection flange that upwardly outwardly extends from said jaw such that blades potentially misdirected towards said slot will be deflected away from the user's hand.

21. The tool of claim 20 wherein both said upper and said lower jaw are provided with a blade deflection flange which flanges cooperate with each other so as to form a radially-shaped hand guard.

22. A tool for safely handling detachable blades of a removable blade scalpel wherein the blades include upper and lower opposed surfaces and an attachment slot, and the scalpel having a handle with a narrow forwardly projecting extension in turn having an upwardly projecting shoulder defined by a pair of inwardly directed longitudinally extending slots along said extension wherein said shoulder is adapted to receive the longitudinally directed attachment slot of a detachable blade, said tool comprising upper and lower longitudinally oriented jaws each having a distal and a proximal end connected for relative motion towards and away from each other to closed and open positions respectively, said lower jaw having a generally planar top surface adapted for engageable receipt of the lower surface of said blade with the distal end of said blade positioned between the proximal end portions of said jaws, said lower jaw being substantially longer than said upper jaw and a slotted recess formed in said lower jaw for receiving and positioning said scalpel handle extension and for positioning said scalpel blade distal end for compressible engagement solely between said upper and lower jaw proximal ends in said closed position thereof, said lower jaw terminating at its outer distal end in a terminal face and said slotted recess extending through said terminal face and extending along a significant portion of said lower jaw, said upper jaw including a cover attached thereto and extending forwardly from said upper jaw distal end over at least a major portion of said lower jaw recess, said cover being at least translucent such that said recess is visible during operation of the tool.

23. A tool for safely handling blades of a removable blade scalpel, said scalpel having a handle with a narrow forwardly projecting extension in turn having an upwardly projecting shoulder defined by a pair of inwardly directed longitudinally extending slots along said extension wherein said shoulder is adapted to receive a longitudinally directed slot of a detachable blade, said blade having upper and lower opposed flat surfaces, said tool comprising upper and lower longitudinally oriented jaws each having a distal and a proximal end and connected for relative motion towards and away from each other to closed and open positions respectively, said lower jaw adapted for engageable receipt of the lower surface of said blade with the distal end of said blade positioned between the proximal end portions of said jaw, said lower jaw being substantially longer than said upper jaw and a recess formed in said lower jaw, said lower jaw receiving and positioning said scalpel blade distal end for compressible engagement solely between said upper and lower jaws in said closed position thereof, said lower jaw terminating at its outer end in a terminal face and said recess extending through said terminal face for receipt of said narrow forwardly projecting extension on said handle.

24. A scalpel blade handling tool comprising a pivotally coupled upper jaw with handle and lower jaw with handle, said jaws with handles longitudinally oriented and capable of relative motion towards and away from each other to closed and open positions respectively, said lower jaw including distal and proximal end portions wherein the distal portion is substantially longer than the upper jaw, said distal end portion also having a longitudinally oriented slot with upwardly projecting side walls on either side of the slot, said proximal end having an engagement surface, the upper jaw also having an engagement surface capable of mutual engagement with the engagement surface on the lower jaw when the lower and upper jaws are moved towards each other to the closed position, said upper jaw including a cover attached thereto and extending forwardly from said upper jaw over at least a major portion of said lower jaw slot, said cover being at least translucent such that said slot is visible during operation of the tool.

25. A tool for safely handling blades attachable to a scalpel handle, said blade having a frontal sharpened end, a centrally located slotted opening in said blade, and a rearward end capable of flexure, said handle slidably engageable with the centrally located slotted opening in said blade for affixing said blade on said handle, said tool comprising a pivotally coupled upper jaw with handle and a lower jaw with handle, said jaws having relative motion towards and away from each other to a closed and open position respectively, the upper jaw having proximal and distal ends and an engagement surface disposed at said proximal end, the lower jaw including a distal end, a central portion, and a proximal end wherein the distal and central portions of the lower jaw are substantially longer than the upper jaw, the distal end of the lower jaw having a longitudinally oriented slot with upwardly projecting side walls on either side of the slot, the proximal end also having an engagement surface capable of mutual engagement with the engagement surface of the upper jaw when the lower and upper jaws are moved towards each other to the closed position.

26. The tool of claim 25, including a pivot arm forwardly extending from said upper jaw and in turn terminating at a frontal pivotal juncture in turn connected to the distal end of said lower jaw such that when the handles are compressed the juncture moves to permit compressible engagement of the upper jaw with the lower jaw to engage a scalpel blade inserted between the upper and lower jaws.

27. The tool of claim 26, said jaws normally biased by the frontal pivotal juncture to a normally open non-blade gripping position.

28. The tool of claim 26 wherein the tool is of integral one piece molded plastic construction.

29. The tool of claim 26 including a cover positioned over the entrance insertion slot on the lower jaw, the cover being at least translucent such that the slot is visible during operation of the tool.

30. The tool of claim 26, said front pivotal juncture in part formed from a part of laterally spaced side arms forwardly extending from the distal end of said upper jaw, said side arms forwardly terminating at a pair of posts in turn upwardly extending from said lower jaw distal end.

31. The tool of claim 25, wherein both said jaw handles are longitudinally oriented.

32. The tool of claim 31, said handles further being essentially superposed in a plane normal to the longitudinal axis.

33. A device for safely handling scalpel blades including:
- a scalpel handle with a narrow forwardly projecting extension with a pair of inwardly directed longitudinally oriented slots;
- a scalpel blade attachable and removable from the handle with a frontal sharpened end, a centrally located slotted opening, and a rearward end capable of flexure to permit slideable engagement and disengagement of the centrally located opening with the slots on the handle; and
- a tool for removing the scalpel blade comprising a lower jaw with a distal end with an alignment slot for receipt of the extension on the handle, a central portion also for receipt of the handle extension and a proximal end for engagement with the frontal sharpened end of the blade when the scalpel blade is inserted into the tool, the tool also having an upper jaw pivotally connected to the lower jaw for mutual engagement with the proximal end of the lower jaw, the upper and lower jaws movable towards and away from each other to a closed and open position respectively, both jaws capable of secure engagement and retention of the frontal sharpened end of the blade while permitting unencumbered flexure of the rearward end of the blade to permit slideable disengagement of the blade from the handle when the upper and lower jaws are moved towards each other to the closed position.

* * * * *